United States Patent [19]

Cauwet et al.

[11] Patent Number: 5,661,118

[45] Date of Patent: Aug. 26, 1997

US005661118A

[54] HAIR AND SKIN WASHING AND TREATMENT COMPOSITIONS BASED ON CERAMIDE AND/OR GLYCOCERAMIDE AND ON POLYMERS CONTAINING CATIONIC GROUPS

[75] Inventors: Daniele Cauwet, Paris; Claude Dubief, Chesnay; Bernard Beauquey, Clichy, all of France

[73] Assignee: L'Oreal, Paris, France

[21] Appl. No.: 427,356

[22] Filed: Apr. 24, 1995

[30] Foreign Application Priority Data

Apr. 22, 1994 [FR] France ............... 94 04880

[51] Int. Cl.⁶ ............... C11D 3/37; C11D 9/36; A61K 7/06; A61K 7/11
[52] U.S. Cl. ............... 510/126; 510/124; 510/123; 510/119; 424/401; 424/DIG. 2
[58] Field of Search ............... 252/544, 549, 252/550, 170; 424/401, 71, DIG. 2; 510/130, 119, 131, 123, 137, 124, 126

[56] References Cited

U.S. PATENT DOCUMENTS

| | | | |
|---|---|---|---|
| 2,261,002 | 10/1941 | Ritter | 260/570 |
| 2,271,378 | 1/1942 | Searle | 167/22 |
| 2,273,780 | 2/1942 | Dittmar | 260/28 |
| 2,337,615 | 12/1943 | McLaren | 180/23 |
| 2,375,853 | 5/1945 | Kirby et al. | 260/583 |
| 2,388,614 | 11/1945 | Kirby et al. | 162/22 |
| 2,454,547 | 11/1948 | Bock et al. | 260/567.6 |
| 2,528,378 | 9/1950 | Mannheimer | 260/309.6 |
| 2,781,354 | 2/1957 | Mannheimer | 260/309.6 |
| 2,961,347 | 11/1960 | Floyd | 117/141 |
| 3,206,462 | 9/1965 | McCarty | 260/256.4 |
| 3,589,578 | 6/1971 | Kamphausen | 226/40 |
| 3,874,870 | 4/1975 | Green et al. | 71/67 |
| 3,929,990 | 12/1975 | Green et al. | 424/78 |
| 3,966,904 | 6/1976 | Green et al. | 424/78 |
| 4,001,432 | 1/1977 | Green et al. | 424/329 |
| 4,005,193 | 1/1977 | Green et al. | 424/168 |
| 4,025,617 | 5/1977 | Green et al. | 424/248.4 |
| 4,025,627 | 5/1977 | Green et al. | 424/325 |
| 4,025,653 | 5/1977 | Green et al. | 260/367.68 P |
| 4,026,945 | 5/1977 | Green et al. | 260/367.68 P |
| 4,027,020 | 5/1977 | Green et al. | 424/248.56 |
| 4,031,307 | 6/1977 | DeMartino et al. | 516/114 |
| 4,131,576 | 12/1978 | Iovine et al. | 260/17.4 |
| 5,194,260 | 3/1993 | Grollier et al. | 424/401 |
| 5,294,444 | 3/1994 | Nakamura et al. | 424/401 |
| 5,368,857 | 11/1994 | Corcoran et al. | 424/401 |
| 5,472,698 | 12/1995 | Rawlings et al. | 424/401 |
| 5,496,489 | 3/1996 | Dussault et al. | 252/134 |
| 5,543,074 | 8/1996 | Hague et al. | 510/122 |

FOREIGN PATENT DOCUMENTS

| | | |
|---|---|---|
| 2 413 907 | 8/1979 | European Pat. Off. . |
| 0 080 976 | 6/1983 | European Pat. Off. . |
| 122324 | 10/1984 | European Pat. Off. . |
| 0 122 324 | 10/1984 | European Pat. Off. . |
| 0 269 243 | 6/1988 | European Pat. Off. . |
| 269243 | 6/1988 | European Pat. Off. . |
| 0278505 | 8/1988 | European Pat. Off. . |
| 1492597 | 9/1966 | France . |
| 1 492 597 | 7/1967 | France . |
| 2 393 573 | 1/1969 | France . |
| 1 583 363 | 10/1969 | France . |
| 2 077 143 | 10/1971 | France . |
| 2 080 759 | 11/1971 | France . |
| 2 137 684 | 12/1972 | France . |
| 2 162 025 | 7/1973 | France . |
| 2080759 | 2/1974 | France . |
| 2 252 840 | 6/1975 | France . |
| 2 270 846 | 1/1976 | France . |
| 2 280 361 | 2/1976 | France . |
| 2 316 271 | 1/1977 | France . |
| 2 320 330 | 3/1977 | France . |
| 2 336 434 | 7/1977 | France . |
| 2 368 508 | 5/1978 | France . |
| 2393573 | 2/1979 | France . |
| 2 470 596 | 6/1981 | France . |
| 2 486 394 | 1/1982 | France . |
| 2 505 348 | 11/1982 | France . |
| 2 519 863 | 7/1983 | France . |
| 2 542 997 | 9/1984 | France . |
| 2 673 179 | 8/1992 | France . |
| WO93/02656 | 2/1993 | WIPO . |
| WO94/03151 | 2/1994 | WIPO . |

*Primary Examiner*—Paul Lieberman
*Assistant Examiner*—Necholus Ogden
*Attorney, Agent, or Firm*—Finnegan, Henderson, Farabow, Garrett & Dunner, L.L.P.

[57] ABSTRACT

Hair and/or skin washing and treatment composition, containing, in a cosmetically acceptable medium:
- at least one anionic surface-active agent,
- at least one amphoteric and/or zwitterionic surface-active agent, these surface-active agents being present in detergent proportions of at least 4% by weight,
- at least one polymer containing cationic groups,
- at least one ceramide and/or one glycoceramide.

27 Claims, No Drawings

HAIR AND SKIN WASHING AND TREATMENT COMPOSITIONS BASED ON CERAMIDE AND/OR GLYCOCERAMIDE AND ON POLYMERS CONTAINING CATIONIC GROUPS

The present invention relates to novel hair and/or skin washing and treatment compositions containing at least one anionic surface-active agent, one amphoteric surface-active agent, one ceramide and/or glycoceramide and one polymer containing cationic groups, and to cosmetic treatment processes using such compositions.

Shampoos having a conditioning effect on the hair are well known in the state of the art, and many of these are based on the use of cationic polymers. Although they are generally of good performance, these shampoos are, however, still considered to be unsatisfactory by those skilled in the art, especially as regards the disentangling of wet hair, and the feel and aesthetic appearance of the dried hair, in particular during the superposition of various treatments.

The inventors have discovered that by using a shampoo containing anionic surface-active agents, amphoteric surface-active agents, polymers containing cationic groups, a ceramide and/or a glycoceramide, a considerable improvement in the cosmetic performance was, surprisingly, observed.

Ceramides and glycoceramides are known per se and have already been recommended in patent FR-A-2,673,179, the disclosure of which is hereby incorporated by reference, especially in shampoos. However, the shampoos differ from the shampoos in accordance with the present invention in that they contain neither amphoteric surface-active agents nor cationic polymers, and they do not lead to the properties observed with the shampoos of the present invention.

The subject of application WO 93/02656, the disclosure of which is hereby incorporated by reference, is cationic dispersions of ceramide and/or of glycoceramide. However, this document does not use cationic polymers.

Compositions which may be shampoos are also known from European Patent EP-A-278,505, the disclosure of which is hereby incorporated by reference, these compositions containing a ceramide or glycoceramide and at least one cholesterol ester in a suitable cosmetic vehicle. The use of amphoteric surface-active agents is never envisaged in this document.

The inventors have more particularly observed a synergy of the disentangling obtained by means of the combination of a polymer containing cationic groups and of a ceramide and/or glycoceramide, in a shampoo containing at least one anionic surfactant and at least one amphoteric and/or zwitterionic surfactant. Improved deposition of the ceramide or of the glycoceramide on the hair was also observed.

According to the invention, the terms "conditioning effect" and "conditioning" refer to an effect which imparts good disentangling properties to the hair, both when wet and when dry, good properties with regard to the feel of the dried hair and an aesthetic appearance, which is a sign of vitality.

The present invention is thus drawn to a hair and/or skin washing and treatment composition based on anionic surface active agents, amphoteric and/or zwitterionic surface-active agents, a polymer containing cationic groups and a ceramide and/or a glycoceramide.

The present invention further relates to a cosmetic treatment process for the hair and/or the skin, which uses such a composition.

Other subjects of the invention will emerge on reading the description and the examples which follow.

The washing and cosmetic treatment composition for the skin and/or the hair, in accordance with the invention, is essentially characterized in that it contains, in a cosmetically acceptable medium:

at least one anionic surface-active agent, at least one amphoteric and/or zwitterionic surface-active agent, the surface-active agents being present in a proportion at least equal to 4% by weight relative to the weight of the composition, at least one polymer containing cationic groups, and at least one ceramide and/or glycoceramide.

The anionic and amphoteric and/or zwitterionic surface-active agents are chosen from surface-active agents having detergent properties. They are used in proportions which are sufficient to impart detergent properties to the composition, i.e., "detergent proportions".

Among the anionic surface-active agents which may be mentioned are the alkali metal salts, ammonium salts, amine salts, amino alcohol salts and magnesium salts of the following compounds: alkyl sulphates, alkyl ether sulphates, alkylamido ether sulphates, alkylaryl polyether sulphates, monoglyceride sulphates; alkylsulphonates, alkylamide sulphonates, alkylarylsulphonates, olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl phosphates, alkyl ether phosphates; acyl sarcosinates, acyl isethionates, N-acyltaurates.

The alkyl or acyl radical of these various compounds generally consists of a carbon chain containing from 12 to 20 carbon atoms.

The aryl radical generally consists of a phenyl or benzyl group.

Among the anionic surface-active agents which may also be mentioned are fatty acid salts such as the salts of oleic acid, ricinoleic acid, palmitic acid and stearic acid; coconut oil acid and hydrogenated coconut oil acid; acyl lactylates, the acyl radical of which contains from 8 to 20 carbon atoms.

It is also possible to use surface-active agents which are generally classified in the family of weakly anionic agents such as alkyl-D-galactosiduronic acids and salts thereof and polyoxyalkylenated carboxylic ether acids and salts thereof, and in particular those containing 2 to 50 ethylene oxide groups.

There may more particularly be mentioned the polyoxyethylenated carboxylic ether acids and acid salts of formula:

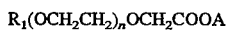

$$R_1(OCH_2CH_2)_nOCH_2COOA$$

in which $R_1$ is an alkyl or alkaryl radical and n has an average value from 2 to 20, the alkyl radical having from 6 to 20 carbon atoms, aryl preferably denoting phenyl, and A denoting hydrogen, an alkali metal or an alkaline-earth metal, an amine or an ammonium.

There may more particularly be mentioned the products sold under the name AKYPO by the company CHEM'Y.

The amphoteric and/or zwitterionic surface-active agents are preferably chosen from aliphatic secondary or tertiary amine derivatives in which the aliphatic radical is a straight or branched chain containing 8 to 18 carbon atoms and containing at least one water-soluble anionic group such as carboxylate, sulphonate, sulphate, phosphate or phosphonate.

Alkyl ($C_8$–$C_{20}$)betaines, sulphobetaines, alkyl ($C_8$–$C_{20}$) amidoalkyl ($C_1$–$C_6$)betaines and alkyl ($C_8$–$C_{20}$) amidoalkyl ($C_1$–$C_6$)sulphobetaines may also be mentioned.

Among the amine derivatives which may be mentioned are the products sold under the name MIRANOL, such as those described in U.S. Pat. Nos. 2,528,378 and 2,781,354, the disclosures of which are hereby incorporated by reference, and classified in the CTFA Dictionary, 5th edition, 1993, under the names "Disodium cocoamphodiacetate" and "Disodium amphocarboxypropionate".

Polymers containing cationic groups are known per se and are preferably chosen from cationic polymers, i.e., from polymers only containing cationic groups, quaternized protein polymers and amphoteric polymers. These polymers are "substantive" polymers which may be revealed using the acidic dye Red 80 according to Richard J. Crawford, Journal of the Society of Cosmetic Chemists, 1980, 31 (5), pages 273 to 278.

These polymers are preferably chosen from the polymers containing primary, secondary, tertiary and/or quaternary amine groups which form part of the polymer chain or which are directly attached to the latter, and which have a molecular weight from 500 to about 5,000,000, and preferably from 1,000 to 3,000,000.

Among these polymers, there may more particularly be mentioned quaternized proteins, polymers of the polyamine, polyamino amide or quaternary polyammonium family, and cationic polysiloxanes.

A) The quaternized proteins are, in particular, chemically modified polypeptides bearing quaternary ammonium groups at the end of the chain or grafted onto the latter. Among these proteins, there may more particularly be mentioned:

collagen hydrolysates bearing triethylammonium groups, such as the products sold under the name "QUATPRO E" via the company Maybrook and referred to in the CTFA dictionary as "Triethonium Hydrolyzed Collagen Ethosulfate".

B) The polymers of the polyamine, polyamino amide or quaternary polyammonium family which may be used in accordance with the present invention are described in particular in the French patents Nos. 2,505,348 and 2,542,997, the disclosures of which are hereby incorporated by reference.

Among these polymers, there may be mentioned:

(1) Quaternized or non-quaternized vinylpyrrolidone/dialkylaminoalkyl acrylate or methacrylate copolymers, such as the products sold under the name "GAFQUAT" by the company GAF Corporation such as, for example "GAFQUAT 734 or 755", or alternatively the products known as "COPOLYMER 845, 958 and 937". These polymers are described in detail in the French patents 2,077,143 and 2,393,573, the disclosures of which are hereby incorporated by reference.

(2) The cellulose ether derivatives containing quaternary ammonium groups described in French patent 1,492,597, the disclosure of which is hereby incorporated by reference and, preferably, the polymers marketed under the names "JR" (JR 400, JR 125, JR 30M) or "LR" (LR 400, LR 30M) by the company Union Carbide Corporation. The polymers are also defined in the CTFA dictionary as hydroxyethylcellulose quaternary ammoniums which have reacted with an epoxide substituted with a trimethylammonium group.

(3) Cationic cellulose derivatives such as the cellulose copolymers or the cellulose derivatives grafted with a water-soluble quaternary ammonium monomer and which are described in greater detail in U.S. Pat. No. 4,131,576, the disclosure of which is hereby incorporated by reference, such as the hydroxyalkylcelluloses, for instance the hydroxymethyl-, hydroxyethyl- or hydroxypropylcelluloses grafted with a methacryloylethyltrimethylaxnrnonium, methacrylamidopropyl trimethylammonium or dimethyldiallylammonium salt.

The marketed products corresponding to this definition are more particularly the products sold under the names "CELQUAT L 200" and "CELQUAT H 100" by the company National Starch.

(4) The quaternized polysaccharides described more particularly in U.S. Pat. Nos. 3,589,578 and 4,031,307, the disclosures of which are hereby incorporated by reference, and more particularly the product marketed under the name "JAGUAR C 13 S" sold by the company Meyhall.

(5) Polymers comprising piperazinyl moieties and of divalent alkylene or hydroxyalkylene radicals containing straight or branched chains, which are optionally interrupted with oxygen, sulphur or nitrogen atoms or with aromatic or heterocyclic rings, as well as the oxidation and/ quaternization products of these polymers. Such polymers are described in the French patents 2,162,025 and 2,280,361, the disclosures of which are hereby incorporated by reference.

(6) Water-soluble polyamino amides prepared in particular by polycondensation of an acidic compound with a polyamine. These polyamino amides may be crosslinked with an epihalohydrine, a diepoxide, a dianhydride, an unsaturated anhydride, a bis-unsaturated derivative, a bis-halohydrine, a bis-azetidinium, a bis-haloacyldiamine, an alkyl bis-halide or alternatively with an oligomer resulting from the reaction of a difunctional compound which is reactive towards a bis-halohydrin, a bis-azetidinium, a bis-haloacyldiamine, an alkyl bishalide, an epihalohydrine, a diepoxide or a bisunsaturated derivative; the crosslinking agent being used in proportions ranging from 0.025 to 0.35 mol per amine group of the polyamino amide.

These polyamino polyamides may be alkylated or, if they contain one or more tertiary amine functions, may be quaternized. Such polymers are described in particular in the French patents 2,252,840 and 2,368,508, the disclosures of which are hereby incorporated by reference.

(7) Polyamino amide derivatives resulting from the coupling of polyalkylene polyamines with polycarboxylic acids followed by an alkylation with difunctional agents. There may be mentioned for example the adipic acid-dialkylaminohydroxyalkyl-dialkylenetriamine polymers in which the alkyl radical contains from 1 to 4 carbon atoms and preferably denotes methyl, ethyl or propyl. Such polymers are described in French patent 1,583,363, the disclosure of which is hereby incorporated by reference.

Among these derivatives, there may more particularly be mentioned the adipic acid/dimethylaminohydroxypropyl/diethylenetriamine polymers sold under the name "CARTARETINE $F,F_4$ or $F_8$" by the company Sandoz.

(8) Polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio of the polyalkylene polyamine to the dicarboxylic acid is from 0.8:1 to 1.4:1; the polyamino amide resulting therefrom is reacted with epichlorohydrin in a molar ratio of epichlorohydrin relative to the secondary amine group of the polyamino amide from 0.5:1 to 1.8:1. Such polymers are described in particular in U.S. Pat. Nos. 2,337,615 and 2,961,347, the disclosures of which are hereby incorporated by reference.

Polymers of this type are marketed in particular under the name "HERCOSETT 57" by the company Hercules Incorporated or alternatively under the name of "PD 170" or "DELSETTE 101" by the company Hercules in the case of the adipic acid/epoxypropyl/diethylenetriamine copolymer.

(9) Methyldiallylamine or dimethyldiallylammonium cyclopolymers having a molecular weight of 20,000 to 3,000,000, such as the homopolymers containing, as main chain constituent, moieties corresponding to the formula (II) or (II'):

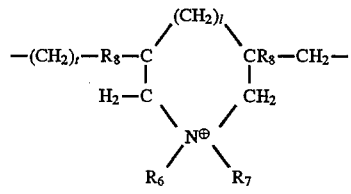

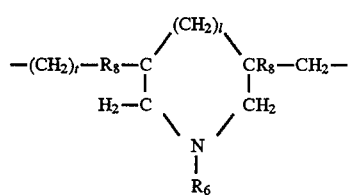

l and t are equal to 0 or 1, and the sum l+t =1;

$R_8$ denotes hydrogen or methyl;

$R_6$ and $R_7$ denote, independently of each other, an alkyl group having from 1 to 22 carbon atoms, a hydroxyalkyl group in which the alkyl group preferably has 1 to 5 carbon atoms, a lower amidoalkyl group and where $R_6$ and $R_7$ may denote, together with the nitrogen atom to which they are attached, heterocyclic groups such as piperidinyl or morpholinyl, as well as copolymers containing units of formula (II) or (II') and units derived from acrylamide or from diacetone acrylamide;

$Y^\ominus$ is an anion such as bromide, chloride, acetate, borate, citrate, tartrate, bisulphate, bisulphite, sulphate or phosphate.

Among the polymers defined above, there may more particularly be mentioned the dimethyldiallylammonium chloride homopolymer sold under the name "MERQUAT 100" having a molecular weight of less than 100,000, the dimethyldiallylammonium chloride and acrylamide copolymer having a molecular weight of greater than 500,000 sold under the names "MERQUAT 550" and "S" by the company Merck.

These polymers are described more particularly in French patent 2,080,759 and the Certificate of Addition thereof No. 2,190,406, the disclosure of which is hereby incorporated by reference.

(10) The quaternary polyammonium polymer containing repeating moieties corresponding to the formula:

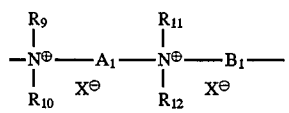

in which $R_9$ and $R_{10}$, $R_{11}$ and $R_{12}$, being identical or different, represent aliphatic, alicyclic or arylaliphatic radicals containing from 1 to 20 carbon atoms or lower hydroxyalkylaliphatic radicals, or alternatively $R_9$ and $R_{10}$ and $R_{11}$ and $R_{12}$, being identical or different, constitute, together or separately, with the nitrogen atoms to which they are attached, heterocycles optionally containing a second hetero atom other than nitrogen, or alternatively $R_9$, $R_{10}$, $R_{11}$ and $R_{12}$, being identical or different, represent a linear or branched $C_1$–$C_6$ alkyl radical substituted with a nitrile, ester, acyl or amide group or a group

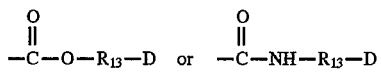

where $R_{13}$ is an alkylene and D is a quaternary axnrnonium group.

$A_1$ and $B_1$ of Formula III represent polymethylene groups containing from 2 to 20 carbon atoms which may be linear or branched and saturated or unsaturated, and which may contain, bonded to or intercalated in the main chain, one or more aromatic rings, or one or more oxygen or sulphur atoms or sulphoxide, sulphone, disulphide, amino, alkylamino, hydroxyl, quaternary ammonium, ureido, amide or ester groups, and $X^\ominus$ denotes an anion derived from an inorganic or organic acid.

$A_1$ and $R_9$ and $R_{11}$ may form, with the two nitrogen atoms to which they are attached, a piperazine ring; in addition, if $A_1$ denotes a saturated or unsaturated linear or branched alkylene or hydroxyalkylene radical, $B_1$ may also denote a group $$(CH_2)_n\text{—CO—D—OC—}(CH_2)_n\text{—}$$

in which D denotes:

a) a glycol residue of formula:

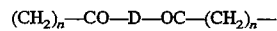

where

Z denotes a linear or branched hydrocarbon radical or a group corresponding to the formulae:

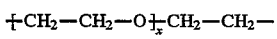

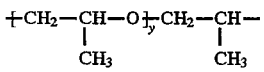

where x and y denote an integer from 1 to 4, representing a defined and single degree of polymerization or any number from 1 to 4 representing an average degree of polymerization;

b) a bis-secondary diamine residue such as a piperazine derivative;

c) a bis-primary diamine residue of formula:

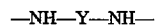

where

Y denotes a linear or branched hydrocarbon radical, or alternatively the divalent radical

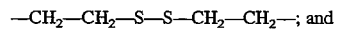; and d) a ureylene group of formula:

—NH—CO—NH—.

$X^{\ominus}$ in Formula III is an anion such as chloride or bromide.

These polymers have a molecular weight generally from 1,000 to 100,000.

Polymers of this type are described in particular in the French patents 2,320,330; 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, the disclosures of all of which are hereby incorporated by reference.

(11) Quaternary polyammonium polymers consisting of moieties of formula (IV):

$$-\underset{\underset{R_{15}}{|}}{\overset{\underset{R_{14}}{|}}{N^\oplus}}-(CH_2)_x-NH-\overset{O}{\overset{\|}{C}}-(CH_2)_m-\overset{O}{\overset{\|}{C}}-NH-(CH_2)_y-\underset{\underset{R_{17}}{|}}{\overset{\underset{R_{16}}{|}}{N^\oplus}}-A- \quad X^\ominus \quad \quad \quad X^\ominus \quad (IV)$$

in which:

$R_{14}$, $R_5$, $R_{16}$ and $R_{17}$, which may be identical or different, represent a hydrogen atom or a methyl, ethyl, propyl, β-hydroxyethyl, β-hydroxypropyl or $-CH_2CH_2(OCH_2CH_2)_pOH$ radical, where p is equal to 0 or an integer from 1 to 6, with the proviso that $R_{14}$, $R_{15}$, $R_{16}$ and $R_{17}$ do not simultaneously represent a hydrogen atom;

x and y, which may be identical or different, are integers from 1 to 6;

m is equal to 0 or to an integer from 1 to 34; x denotes a halogen atom;

A denotes a radical of a dihalide and preferably represents the residue:

$$-CH_2-CH_2-O-CH_2-CH_2-$$

Such compounds are described in greater detail in European Patent Application EP-A-122,324, the disclosure of which is hereby incorporated by reference.

There may, for example, be mentioned among these, the products "MIRAPOL A 15", "MIRAPOL AD1", "MIRAPOL AZ1" and "MIRAPOL 175" sold by the company Miranol.

(12) Homopolymers or copolymers derived from acrylic or methacrylic esters or amides and containing the moieties:

$$-CH_2-\underset{\underset{\underset{\underset{/\;\backslash}{N}}{\underset{A_2}{|}}}{\underset{O}{|}}}{\overset{R_{20}}{\underset{|}{C}}}-\quad,\quad -CH_2-\underset{\underset{\underset{R_{21}-\overset{\oplus}{N}-R_{23}}{\underset{A_2}{|}}}{\underset{O}{|}}}{\overset{R_{20}}{\underset{|}{C}}}-\quad or\quad -CH_2-\underset{\underset{\underset{R_{21}-\overset{\oplus}{N}-R_{23}}{\underset{A_2}{|}}}{\underset{NH}{|}}}{\overset{R_{20}}{\underset{|}{C}}}- \quad (V)$$

$R_{18}\quad R_{19} \qquad\qquad R_{22}\;\; X_2^\ominus \qquad R_{22}\;\; X_2^\ominus$ in which:

$R_{20}$ denotes H or $CH_3$;

$A_2$ is a linear or branched alkyl group of 1 to 6 carbon atoms or a hydroxyalkyl group of 1 to 4 carbon atoms;

$R_{21}$, $R_{22}$ and $R_{23}$, which may be identical or different, represent an alkyl group having from 1 to 18 carbon atoms or a benzyl radical;

$R_{18}$ and $R_{19}$, which can be identical or different, represent hydrogen or an alkyl group having from 1 to 6 carbon atoms;

$X^\ominus_2$ denotes a methosulphate anion or a halide such as chloride or bromide.

The comonomer or comonomers which may be used belong to the family of acrylamide, methacrylamide, diacetone acrylamide, acrylamide and methacrylamide substituted at the nitrogen with lower alkyls, of acrylic acid or methacrylic acid or esters thereof, vinylpyrrolidone, or of vinyl esters.

Among these compounds, there may be mentioned the acrylamide and dimethylaminoethyl methacrylate copolymer quaternized with dimethyl sulphate and sold under the name "HERCOFLOC" by the company Hercules, the acrylamide and methacryloyloxyethyltrimethylammonium chloride copolymer—described in European Patent Application EP-A-80,976, the disclosure of which is hereby incorporated by reference, and sold under the name "BINA QAT P100" by the Company Ciba Geigy, or alternatively poly (methacrylamidopropyl trimethylammonium chloride) sold under the name "POLYMAPTAC" by the company Texaco Chemicals, methacryloyloxyethyltrimethylammonium methosulphate and the copolymer thereof with acrylamide, which are sold under the name "RETEN" by the company Hercules.

(13) Quaternary polymers of vinylpyrrolidone and of vinylimidazole such as, for example, the products marketed under the names "LUVIQUAT FC 905, FC 550 and FC 370" by the company BASF.

(14) Polyamines such as Polyquart H sold by Henkel, and referred to under the name "POLYETHYLENE GLYCOL (15) TALLOW POLYAMINE" in the CTFA dictionary.

(15) Cross linked polymers of methacryloyloxyethyltrimethylammonium chloride such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or the co-polymerization being followed by a crosslinking with a compound containing olefinic unsaturation, in particular methylenebis (acrylamide).

An acrylamide/methacryloyloxyethyltrimethyl ammonium chloride crosslinked copolymer (20/80 by weight) in the form of a dispersion containing 50% by weight of the said copolymer in mineral oil is more particularly used. This dispersion is marketed under the name SALCARE SC92 by the company Allied Colloids. A methacryloyloxyethyltrimethylammonium chloride crosslinked homopolymer containing approximately 50% by weight of the homopolymer in mineral oil is also used. This dispersion is marketed under the name SALCARE SC95 by the company Allied Colloids.

Other cationic polymers which may be used in accordance with the invention are polyalkyleneimines, in particular polyethyleneimines, polymers containing vinylpyridine or vinylpyridinium moieties, condensates of polyamines and epichlorohydrin, quaternary polyureylenes and chitin derivatives, and cationic polysiloxanes.

The amphoteric polymers are preferably polymers containing moieties A and B which are statistically distributed in the polymer chain, where A denotes a moiety derived from a monomer containing at least one basic nitrogen atom and B denotes a moiety derived from an acidic monomer containing one or more carboxylic or sulphonic groups or alternatively A and B may denote groups derived from carboxybetaine zwitterionic monomers; A and B may also denote a cationic polymer chain containing primary, secondary, tertiary or quaternary amine groups in which at least one of the amine groups bears a carboxylic or sulphonic group which is attached via a hydrocarbon radical or alternatively A and B form part of a chain of a polymer containing ethylene α-β-dicarboxylic moieties in which one of the carboxylic groups has been reacted with a polyamine containing one or more primary or secondary or tertiary amine groups.

Such polymers are described especially in the French patents FR-2,470,596, FR-2,486,394 and FR-2,519,863, the disclosures of which are hereby incorporated by reference.

There may in particular be mentioned the polymers derived from chitosan which are chosen in particular from those described in French patent 2,137,684, the disclosure of which is hereby incorporated by reference, and containing moieties corresponding to the formulae (VI):

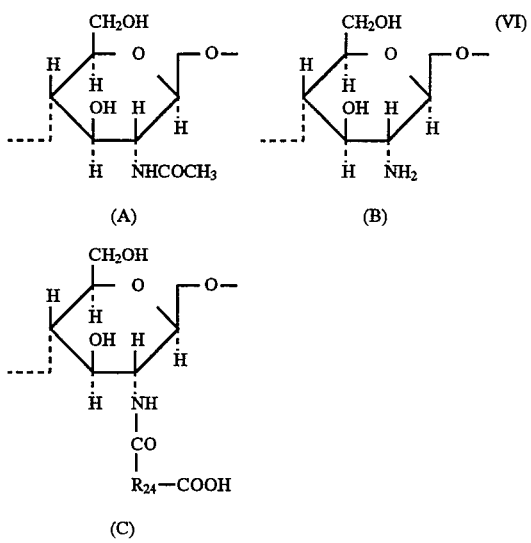

The moiety (A) is present in proportions from 0 to 30%, the moiety (B) from 5 to 50%, the moiety (C) from 30 to 90% by weight. $R_{24}$ represents a linear or branched alkylene group containing from 2 to 5 carbon atoms.

The preferred polymer preferably contains 0 to 20% of moiety (A), 40 to 50% of moiety (B) and 40 to 50% of moiety (C) in which $R_{24}$ denotes an alkylene radical and preferably —$CH_2$—$CH_2$—.

The polymers derived from diallyldialkylammonium and an anionic monomer such as, more particularly, the polymers containing from 60 to approximately 99% by weight of unit derived from a quaternary diallyldialkylammonium monomer, in which the alkyl groups are chosen independently from alkyl groups having 1 to 18 carbon atoms and in which the anion is derived from an acid which has an ionization constant greater than 10—13 and 1 to 40% by weight of this polymer of an anionic monomer chosen from acrylic acid or methacrylic acid, the molecular weight of this polymer being approximately from 50,000 to 10,000,000 determined by gel permeation chromatography and described in particular in Application EP-A-269,243, the disclosure of which is hereby incorporated by reference.

Among these polymers, there may more particularly be mentioned the copolymer of dimethyldiallylammonium-chloride and of diethyldiallylammonium chloride and of acrylic acid.

More particularly preferred products are the products sold under the name "MERQUAT 280" by the company Calgon in the form of an aqueous solution containing 35% of active materials, this polymer being a copolymer of diallyldim-ethylammonium chloride and acrylic acid in proportions of 80/20, the viscosity on a Brookfield LVF module 4 viscometer being from 4,000 to 10,000 cps, the molecular weight being approximately equal to 1,300,000.

The polymers preferably used, in accordance with the invention, are, in particular, the quaternary cellulose ether derivatives such as the products sold under the name "JR 400" by the company Union Carbide Corporation, cyclopolymers, in particular the dimethyldiallylaxnmonium chloride and acrylamide copolymers having a molecular weight greater than 500,000, which are sold under the names "MERQUAT 550" and "MERQUAT S" by the company Merck or the diallyldimethylammonium chloride and acrylic acid copolymer marketed under the name '1MERQUAT 280" by the company Calgon.

Cationic polysaccharides and more particularly the polymer sold under the name "JAGUAR C13S" by the company Meyhall.

The ceramides and/or glycoceramides are known per se and are natural or synthetic molecules corresponding to the general formula (VII):

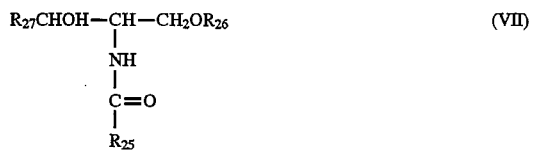

in which:

$R_{25}$ denotes a saturated or unsaturated linear or branched alkyl radical derived from $C_{14}$–$C_{30}$ fatty acids, it being possible for this radical to be substituted with a hydroxyl group in the α-position or a hydroxyl group in the ω-position which is esterified with a saturated or unsaturated $C_{16}$–$C_{30}$ fatty acid;

$R_{26}$ denotes a hydrogen atom or a (glycosyl)$_n$, (galactosyl)$_m$ or sulphogalactosyl radical;

in which:

n is an integer ranging from 1 to 4; and m is an integer ranging from 1 to 8;

$R_{27}$ denotes a saturated or unsaturated $C_{15}$–$C_{26}$ hydrocarbon radical in the α-position which may be substituted with one or more $C_1$–$C_{14}$ alkyl radicals;

in the case of natural ceramides or glycoceramides, $R_{27}$ may also denote a $C_{15}$–$C_{26}$α-hydroxyalkyl radical, the hydroxyl group optionally being esterified with a $C_{16}$–$C_{30}$ α-hydroxy acid.

The preferred ceramides are those described by Downing in Arch. Dermatol, vol. 123, 1381–1384, 1987, or those described in French patent FR-2,673,179, the structures of which may be as follows:

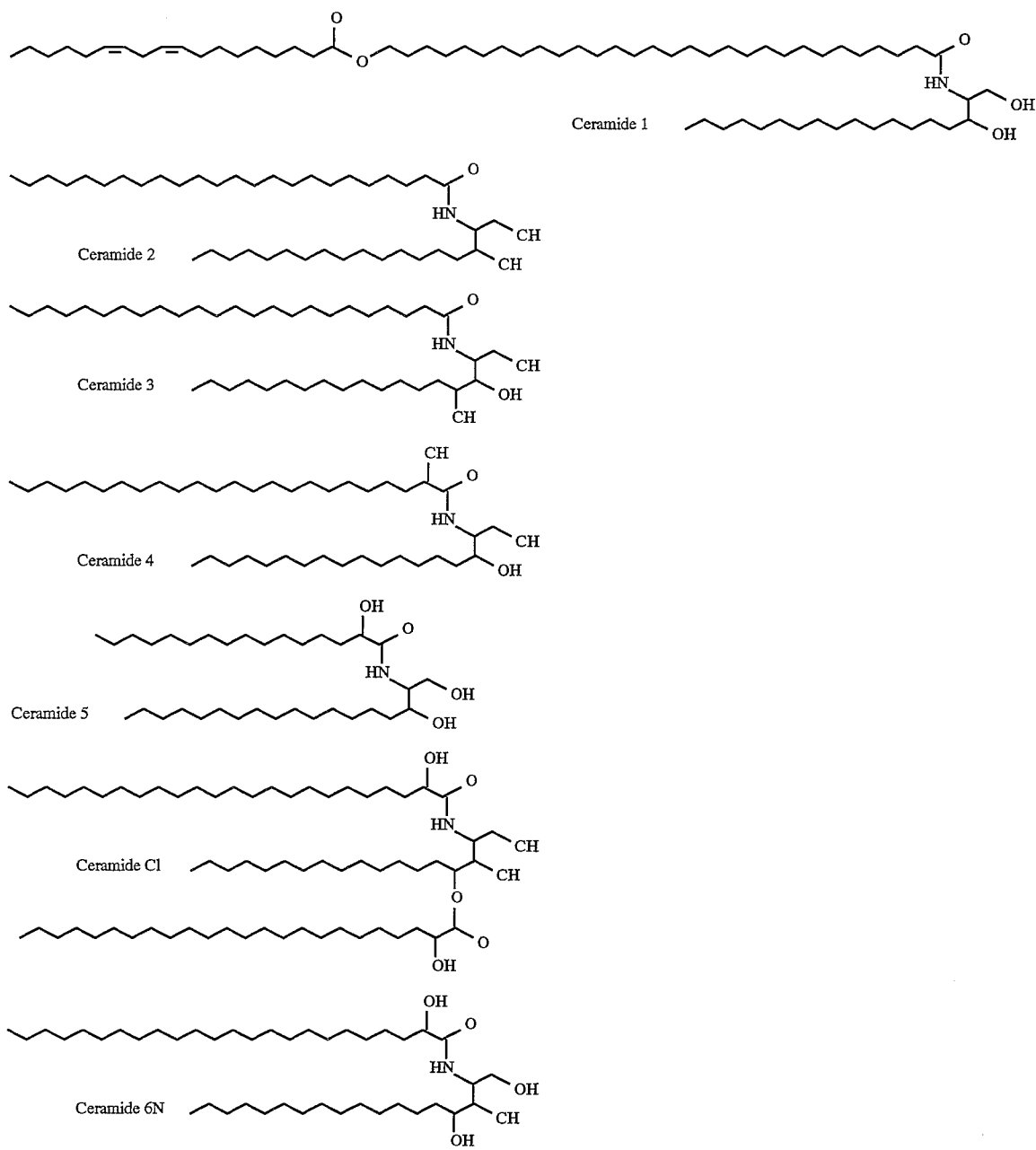

The ceramides more particularly preferred are the compounds of formula (VII) for which:
R$_{25}$ denotes a saturated or unsaturated alkyl derived from C$_{16}$–C$_{22}$ fatty acid;
R$_{26}$ denotes hydrogen;
R$_{27}$ denotes a saturated linear C$_{15}$ radical.

Such compounds are, for example:
N-linoleoyldihydrosphingosine,
N-oleoyldihydrosphingosine,
N-palmitoyldihydrosphingosine,
N-stearoyldihydrosphingosine,
N-behenoyldihydrosphingosine,
or mixtures of these compounds.

Those compounds for which:
R$_{25}$ denotes a saturated or unsaturated alkyl radical derived from fatty acid;
R$_{26}$ denotes galactosyl or sulphogalactosyl; and
R$_{27}$ denotes —CH=CH—(CH$_2$)$_{12}$—CH$_3$
are also preferably used There may be mentioned the product consisting of a mixture of these compounds, which is sold under the brand name GLYCOCER by the company Waitaki International Biosciences.

In accordance with the invention, the detergent surface-active agents (anionic, amphoteric, zwitterionic) are present in proportions greater than 4% and generally less than 60%.

The anionic surface-active agents are used in proportions from 3 to 50% by weight relative to the total weight of the composition, and preferably from 5 to 30% by weight.

The amphoteric and/or zwitterionic surface-active agents are preferably present in proportions from 1 to 50% by weight and preferably from 1.5 to 15% by weight.

The cationic polymers are preferably used in proportions from 0.05 to 5% by weight, expressed as active material, and preferably from 0.1 to 3% by weight, relative to the total weight of the composition.

The ceramides and/or glycoceramides are preferably used in proportions from 0.005 to 5% by weight, expressed as active material, and preferably from 0.01 to 3% by weight, relative to the total weight of the composition.

The pH of the compositions is preferably from 2 to 9 and more preferably from 3 to 8. It is adjusted using cosmetically acceptable basifying or acidifying agents.

The compositions in accordance with the invention may contain other adjuvants usually used in hair and/or skin washing and conditioning compositions.

These compositions may especially contain well-known nonionic surface-active agents which may be chosen from polyethoxylated, polypropoxylated or polyglycerolated alcohols, α-diols, alkylphenols and fatty acids, having a fatty chain containing, for example, 8 to 18 carbon atoms, it being possible for the number of ethylene oxide and of propylene oxide groups to range in particular from 2 to 50 and the number of glycerol groups to range especially from 2 to 30. There may also be mentioned the copolymers of ethylene oxide and of propylene oxide, the condensates of ethylene oxide and of propylene oxide with fatty alcohols; polyethoxylated fatty amides preferably having 2 to 30 mol of ethylene oxide, polyglycerolated fatty amides containing on average 1 to 5 glycerol groups and preferably 1.5 to 4 glycerol groups; polyethoxylated fatty amines preferably having 2 to 3 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, Nalkylglucamine derivatives, amine oxides such as alkyl ($C_{10}$–$C_{14}$) amine oxides or N¯acylaminopropylmorpholine oxides. The alkylpolyglycosides and the polyglycerolated fatty acid alcohols, α-diols and alkylphenols are more particularly preferred.

The compositions may also contain thickening agents chosen in particular from sodium alginate, gum arabic, cellulose derivative such as methylcellulose, hydroxymethylcellulose, hydroxyethylcellulose, hydroxypropylcellulose and hydroxypropylmethylcellulose, guar gum or derivatives thereof, xanthan gums, scleroglucans, crosslinked polyacrylic acids, polyurethanes, copolymers based on maleic acid or on maleic anhydride, associative thickeners bearing fatty chains of natural type for instance the product marketed under the name NATROSOL PLUS, or of synthetic type, for instance the products marketed under the name PEMULEN.

The thickening may also be obtained by mixing polyethylene glycol and polyethylene glycol stearates or distearates or by mixing phosphoric esters and amides.

The cosmetically acceptable medium preferably comprises water, but may also contain cosmetically acceptable solvents such as monoalcohols, polyalcohols, glycol ethers or fatty acid esters, which are used alone or as a mixture. Among these solvents, there may more particularly be mentioned lower alcohols such as ethanol and isopropanol, polyalcohols such as ethylene glycol and diethylene glycol, glycol ethers, glycol alkyl ethers or diethylene glycol alkyl ethers.

The compositions in accordance with the invention may also contain dyes, viscosity-modifying agents, nacreous agents, hydrating agents, anti-dandruff agents, anti-seborrhoeic agents, sunscreen agents, proteins, vitamins, α-hydroxy acids, salts, fragrances, preserving agents, sequestering agents, softening agents, foam modifiers and detoxifying agents.

Conditioning agents other than the cationic polymers may also be used. There may be mentioned linear or branched (saturated or unsaturated) cyclic or aliphatic hydrocarbon, synthetic or non-synthetic, hydrogenated or unhydrogenated natural oils, soluble or insoluble volatile or non-volatile silicones which may or may not be organically modified, fluorinated or perfluorinated oils, polybutenes and polyisobutenes, fatty esters in liquid, pasty or solid form, esters of polyhydric alcohols, glycerides, natural or synthetic waxes, silicone gums and resins, or the mixture of these various agents. The compositions in accordance with the invention are more particularly used for washing the hair and/or the skin and are in the form of fluid or thickened liquids, gels or creams.

They may be used as they are or they may be diluted before use. They may be used with the aid of a pressurized container and may be delivered in the form of a liquid, a cream, a gel or a foam.

The examples which follow are intended to illustrate the invention without, however, having a limiting nature.

EXAMPLES

Examples 1 to 7

|  | 1 | 2* | 3* | 4 | 5* | 6 | 7* |
|---|---|---|---|---|---|---|---|
| Sodium lauryl ether sulphate | 8 g AM | 8 | 8 | 8 | 8 | 8 | 8 |
| Cocoyl betaine | 4 g AM | 4 | 4 | 4 | 4 | 4 | 4 |
| MERQUAT 550 | 0.5 g | 0.7 g | — | — | — | — | — |
| SALCARE SC 92 | — | — | — | 0.5 | 0.7 | — | — |
| JAGUAR C13S | — | — | — | — | — | 0.5 | 0.7 |
| CERAMIDE A | 0.2 g | — | 0.7 g | 0.2 g | — | 0.2 g | — |
| Preserving agents | 0.1 | 0.1 | 0.1 | 0.1 | 0.1 | 0.1 | 0.1 |
| Water qs | 100 g | 100 g | 100 g | 100 g | 100 g | 100 g | 100 g |
| pH adjusted NaOH | 6.5 | 6.5 | 6.5 | 6.5 | 6.5 | 6.5 | 6.5 |

Examples 2, 3, 5 and 7 were not in accordance with the invention, i.e., they were comparative examples.

1 g of shampoo was applied to wet hair. After leaving the shampoo in place for a period of 5 minutes, the hair was rinsed with running water.

3 locks of hair were tested for each formulation of Examples 1–7. A panel of 10 testers was asked to classify the 3 locks relating to each association on the basis of the ease of disentangling and the softness of the wet hair.

For each association, the 10 testers determined that: the compositions of Examples 1, 4 and 6 were easier to disentangle and softer than the corresponding compositions not containing either the cationic polymer (Example 3) or the ceramide (Examples 2, 5 and 7).

Ceramide A

N-oleoyldihydrosphingosine of formula:

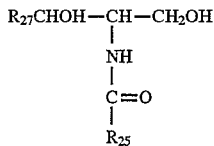

in which:

$R_{27}$=CHOH—CH—CH$_2$OH $R_{25}$=C$_{17}$H$_{33}$

MIRQUAT 550 (sold by the company Merck): dimethyldiallylammonium chloride and acrylamide copolymer (=polyquaternium-7) (CTFA)

SALCARE SC 92 (sold by the company Allied Colloid) Dispersion in mineral oil of acrylamide/methacryloyloxyethyltrimethylammonium chloride cross linked copolymer, sold at a copolymer content of 50% (=polyquaternium-32) (CTFA)

JAGUAR C 13 S (sold by the company Meyhall) Hydroxypropyl guar gum quaternized with 2,3-epoxypropyltrimethylammonium chloride.

Examples 8 to 11

|  | 8 | 9* | 10 | 11* |
|---|---|---|---|---|
| Sodium lauryl ether sulphate | 8 | 8 | 8 | 8 |
| Cocoyl betaine | 4 | 4 | 4 | 4 |
| JR 400 | 0.5 | 0.7 |  |  |
| POLYMER A |  |  | 0.5 | 0.7 |
| CERAMIDE A | 0.2 |  | 0.2 |  |
| Preserving agents | 0.1 | 0.1 | 0.1 | 0.1 |
| Water qs | 100 g | 100 g | 100 g | 100 g |
| pH adjusted | 6.5 | 6.5 | 6.5 | 6.5 |

*Examples 9 and 11 were not in accordance with the invention.

The process was performed as described above and it was again observed that the locks treated with the shampoos of Examples 8 and 10 were easier to disentangle and felt softer than the locks treated with the shampoos of Examples 9, 11 and 3 respectively.

Polymer A

Polymer containing moieties of formula:

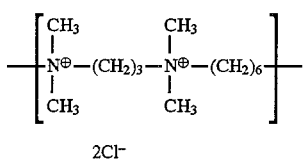

prepared and described in French patent No. 2,270,846.

JR 400 (sold by the company Amerchol) Hydroxyethylcellulose and epichlorohydrin polymer quaternized with trimethylamine (=polyquaternium-10) (CTFA).

Example 12

The following composition was prepared:

| Sodium lauryl ether sulphate containing 2.2 mol of ethylene oxide as a 28% aqueous solution, sold under the name "EMPICOL ESB/3 FL" by the company Albright and Wilson | 10 g AM |
|---|---|
| Sodium lauryl ether carboxylate (C$_{12}$/C$_{14}$ 70–30) containing 4.5 mol of ethylene oxide as a 22% aqueous solution, sold under the name "AKYPOSOFT 45 NV" by the company CHEM'Y | 3 g AM |
| Cocoamidopropylbetaine | 7 g |
| Ceramide A | 0.4 g |
| Polyquaternium-7 | 0.1 g |
| Preserving agent, fragrance | |
| Water qs | 100 g |
| pH adjusted to 5 with HCl | |

This composition was used as a shower gel.

Example 13

The following composition was prepared:

| Sodium lauryl ether sulphate containing 2.2 mol of ethylene oxide as a 28% aqueous solution, sold under the name "EMPICOL ESB/3 FL" by the company Albright and Wilson | 8 g AM |
|---|---|
| Cocoylbetaine as a 32% aqueous solution | 4 g AM |
| Ceramide A | 0.1 g |
| Guar hydroxypropyltriamonium chloride | 0.4 g |
| Preserving agents, fragrance | |
| Water qs | 100 g |
| pH adjusted to 6.9 with HCl | |

This composition was used as a shampoo.

Example 14

The following composition was prepared:

| Sodium lauryl ether sulphate and magnesium lauryl ether sulphate (80/20) containing 4 mol of ethylene oxide, sold under the name "EMPICOL BSD" by the company Albright and Wilson at an active material content of 26% | 10 g AM |
|---|---|
| Cocoylamidopropylbetaine/glyceryl mono laurate mixture (25/5), sold under the name "TEGOBETAINE HS" by the company Goldschmidt at an active material content of 30% | 3 g AM |
| Ceramide A | 0.2 g |
| Polyquaternium-10 | 0.5 g |
| Preserving agents, fragrance | |
| Water qs | 100 g |
| pH adjusted to 7.2 with NaOH | |

This composition was used as a shampoo.

What is claimed is:

1. A washing and treatment composition for hair, skin, or hair and skin, comprising, in a cosmetically acceptable medium:

at least one anionic surface-active agent, and at least one surface-active agent selected from zwitterionic and amphoteric surface-active agents, said surface-active agents being present in detergent proportions equal to at least 4% and less than 60% by weight, at least one polymer containing cationic groups, wherein said at least one polymer has a molecular weight of 500 to 5,000,000, and at least one compound selected from ceramides and glycoceramides.

2. A composition according to claim 1, wherein said at least one anionic surface active agent is selected from the salts of the following compounds: alkali metals, ammonium, amines, amino alcohols, alkylsulphonates, alkylamide sulphonates, alkylarylsulphonates, olefin sulphonates, paraffin sulphonates, alkyl sulphosuccinates, alkyl ether sulphosuccinates, alkylamide sulphosuccinates, alkyl sulphosuccinamates, alkyl sulphoacetates, alkyl phosphates, alkyl ether phosphates, acyl sarcosinates, acyl isethionates, N-acyltaurates;

magnesium salts of the following: alkyl sulphates, alkyl ether sulphates, alkylamido ether sulphates, alkylaryl polyether sulphates, monoglyceride sulphates;

fatty acid salts, coconut oil acid, hydrogenated coconut oil acid, acyl lactylates, alkyl-D-galactosiduronic acids and salts thereof, and polyoxyalkylenated carboxylic ether acids.

3. A composition according to claim 1, wherein said at least one amphoteric surface-active agent, at least one zwitterionic surface-active agent, or at least one amphoteric surface-active agent and at least one zwitterionic surface-active agent is selected from aliphatic secondary and tertiary amide compounds in which the aliphatic radical is a linear or branched chain containing 8 to 18 carbon atoms and containing at least one water-soluble anionic group.

4. A composition according to claim 1, wherein said at least one polymer containing cationic groups is selected from substantive polymers containing at least one amine group, said at least one amine group being selected from primary, secondary, tertiary, and quaternary amine groups, said at least one amine group forming part of the polymer chain or being directly attached thereto; amphoteric polymers; and quaternized proteins, and said at least one polymer having a molecular weight ranging from about 500 to 5,000,000.

5. A composition according to claim 4, wherein said at least one polymer containing cationic groups is selected from quaternized proteins comprising chemically modified polypeptides bearing quaternary ammonium groups at the end of the chain of said polypeptides or grafted onto said chain.

6. A composition according to claim 4, wherein said at least one polymer containing cationic groups is selected from polyamines, polyamino amides, and quaternary polyammoniums, which are selected from:

(1) quaternized or non-quaternized vinylpyrrolidone/ dialkylaminoalkyl acrylate or methacrylate copolymers;

(2) cellulose ether derivatives containing quaternary ammonium groups;

(3) cationic cellulose derivatives comprising cellulose polymers or of cellulose derivatives grafted with a water-soluble quaternary ammonium monomer;

(4) quaternized polysaccharides;

(5) polymers comprising piperazinyl moieties and divalent alkylene or hydroxyalkylene radicals containing straight or branched chains, which are optionally interrupted with oxygen, sulphur or nitrogen atoms or with aromatic or heterocyclic rings, as well as the oxidation and quaternization products of these polymers;

(6) water-soluble polyamino amides which are optionally crosslinked, alkylated, or crosslinked and alkylated;

(7) polyamino amide derivatives resulting from the condensation of polyalkylene polyamines with polycarboxylic acids followed by alkylation of the difunctional agents;

(8) polymers obtained by reaction of a polyalkylene polyamine containing two primary amine groups and at least one secondary amine group with a dicarboxylic acid;

(9) cyclopolymers having a molecular weight of 20,000 to 3,000,000, of methyldiallylamine or of dimethyldiallylammonium;

(10) crosslinked polymers of methacryloyloxyethyltrimethylammonium chloride;

(11) quaternary polyammonium polymers;

(12) homopolymers or copolymers derived from acrylic or methacrylic esters or amides;

(13) quaternary polymers of vinylpyrrolidone and of vinylimidazole;

(14) polyamines;

(15) polyalkylene imines;

(16) polymers containing vinylpyridine or vinylpyridinium moieties;

(17) condensates of polyamines and epichlorohydrin;

(18) polyureylenes; and

(19) chitin derivatives.

7. A composition according to claim 4, wherein said at least one polymer containing cationic groups is selected from amphoteric polymers containing moieties A and B which are statistically distributed in the polymer chain, where A denotes a moiety derived from a monomer containing at least one basic nitrogen atom and B denotes a moiety derived from an acidic monomer containing one or more carboxylic or sulphonic groups; alternatively A and B may denote groups derived from carboxybetaine zwitterionic monomers; A and B may also denote a cationic polymer chain containing primary, secondary, tertiary or quaternary amine groups in which at least one of the amine groups bears a carboxylic or sulphonic group which is attached to the chain via a hydrocarbon radical or alternatively A and B form part of a chain of a polymer containing ethylene α,β-dicarboxylic moieties in which one of the carboxylic groups has been reacted with a polyamine containing one or more primary or secondary or tertiary amine groups.

8. A composition according to claim 7, wherein said amphoteric polymers are selected from polymers derived from chitosan, containing moieties corresponding to the formulae (VI):

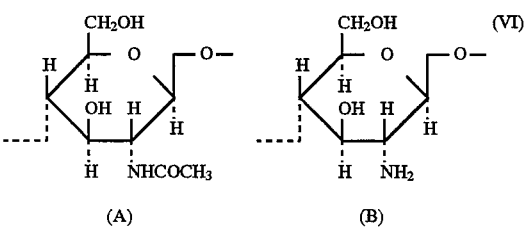

-continued

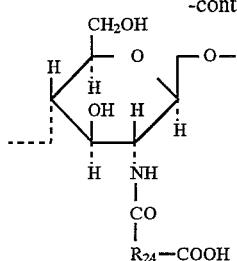

(C)

in which the moiety (A) is present in proportions from 0 to 30%, the moiety (B) from 5 to 50%, the moiety (C) from 30 to 90% by weight, $R_{24}$ representing a linear or branched alkylene chain of 2 to 5 carbon atoms, the polymers derived from diallyldialkylammonium and an anionic monomer are selected from acrylic acid and methacrylic acid.

9. A composition according to claim 1, wherein said at least one ceramide, at least one glycoceramide, or at least one ceramide and at least one glycoceramide is selected from the compound of general formula:

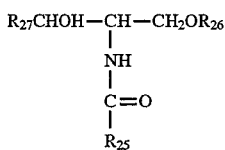

in which $R_{25}$ denotes a saturated or unsaturated or unsaturated linear or branched alkyl radical derived from $C_{14}$–$C_{30}$ fatty acids, said radical being optionally substituted with a hydroxy group in the α-position, the hydroxyl group being esterified with a saturated or unsaturated $C_{16}$–$C_{30}$ fatty acid, or a hydroxyl group in the ω-position, the hydroxyl group being esterified with a saturated or unsaturated $C_{16}$–$C_{30}$ fatty acid; $R_{26}$ denotes a hydrogen atom or a (glycosyl)$_n$, (galactosyl)$_m$ or sulphagalactosyl radical; where n is an integer ranging from 1 to 4; and m is an integer ranging from 1 to 8; $R_{27}$ denotes a saturated or unsaturated $C_{15}$–$C_{26}$ hydrocarbon radical in the α-position which may be substituted with one or more $C_1$–$C_{14}$ alkyl radicals; in the case of natural ceramides or glycoceramides, $R_{27}$ may also denote a $C_{15}$–$C_{26}$ α-hydroxyalkyl radical, the hydroxyl group optionally being esterified with a $C_{16}$–$C_{30}$ α-hydroxy acid.

10. A composition according to claim 1, wherein said at least one anionic and said at least one amphoteric surface-active agent, said at least one zwitterionic surface-active agent, or said at least one amphoteric surface-active agent and said at least one zwitterionic surface-active agent are present in a combined amount of less than 60% by weight relative to the weight of the composition.

11. A composition according to claim 10, wherein said at least one anionic surface-active agent is present in a proportion of from 3 to 50% by weight, relative to the total weight of the composition.

12. A composition according to claim 11, wherein said at least one anionic surface-active agent is present in a proportion of from 5 to 30% by weight, relative to the total weight of the composition.

13. A composition according to claim 11, wherein said at least one amphoteric surface-active agent, said at least one zwitterionic surface-active agent, or said at least one amphoteric surface-active agent and said at least one zwitterionic surface-active agent is present in a proportion of from 1 to 50% by weight, relative to the total weight of the composition.

14. A composition according to claim 13, wherein said at least one amphoteric surface-active agent, said at least one zwitterionic surface-active agent, or said at least one amphoteric surface-active agent and said at least one zwitterionic surface-active agent is present in a proportion of from 1.5 to 15% by weight, relative to the total weight of the composition.

15. A composition according to claim 1, wherein said at least one polymer containing cationic groups is present in a proportion of from 0.05 to 5% by weight, expressed as active material.

16. A composition according to claim 15, wherein said at least one polymer containing cationic groups is present in a proportion of from 0.1 to 3% by weight, relative to the total weight of the composition.

17. A composition according to claim 1, wherein said at least one, ceramide, at least one glycoceramide, or at least one ceramide and at least one glycoceramide is present in a proportion ranging from 0.005 to 5% by weight, relative to the total weight of the composition.

18. A composition according to claim 17, wherein said at least one ceramide, at least one glycoceramide, or at least one ceramide and at least one glycoceramide is present in a proportion ranging from 0.01 to 3% by weight, relative to the total weight of the composition.

19. A composition according to claim 1, wherein the pH of said composition ranges from 2 to 9.

20. A composition according to claim 1, wherein said composition further comprises nonionic surface-active agents.

21. A composition according to claim 1, wherein said composition further comprises thickening agents.

22. A composition according to claim 1, wherein said cosmetically acceptable medium comprises water or a mixture of water and at least one cosmetically acceptable solvent selected from monoalcohols, polyalcohols, glycol ethers and fatty acid esters.

23. A composition according to claim 1, wherein said composition further comprises preserving agents, sequestering agents, softening agents, foe modifiers, dyes, viscosity-modifying agents, nacreous agents, hydrating agents, anti-dandruff agents, antiseborrhoeic agents, sunscreen agents, proteins, vitamins, α-hydroxy acids, salts, detoxifying agents, fragrances or mixtures thereof.

24. A composition according to claim 1, wherein said composition further comprises other conditioning agents selected from saturated or unsaturated linear or branched cyclic or aliphatic synthetic or non-synthetic, hydrogenated or unhydrogenated natural oils; volatile or non-volatile silicones which may or may not be organically modified and which may or may not be soluble in the medium; fluorinated or perfluorinated oils; polybutenes; polyisobutenes; fatty esters; esters of polyhydric alcohols; glycerides; natural or synthetic waxes; proteins; and mixtures of these.

25. A composition according to claim 1, wherein said composition is in the form of a fluid or thickened liquid, a gel, a cream or a foam, optionally packaged under pressure.

26. A method for washing and conditioning the hair, comprising the steps of applying to the hair a composition according to claim 1; optionally leaving the composition in place for a period of time; and rinsing the hair.

27. A method of washing the skin or the hair, comprising the steps of applying to the skin or the hair a composition according to claim 1; and optionally rinsing the skin or the hair.

* * * * *

UNITED STATES PATENT AND TRADEMARK OFFICE
CERTIFICATE OF CORRECTION

PATENT NO.: 5,661,118

DATED: August 26, 1997

INVENTOR(S): Daniele CAUWET; Claude DUBIEF; Bernard BEAUGUEY

It is certified that an error appears in the above-identified patent and that said Letters Patent is hereby corrected as shown below:

In Claim 3, Col. 17, line 22, delete "amphoteric"; and after "agent", insert --selected from zwitterionic and amphoteric surface-active agents--;

lines 22-25, delete ", at least one zwitterionic surface-active agent, or at least one amphoteric surface-active agent and at least one zwitterionic surface-active agent";
line 25, before "selected", insert --further.

In Claim 9, Col. 19, lines 21-22, "ceramide, at least one glycoceramide, or at least one ceramide and at least one glycoceramide" should read --compound selected from ceramides and glycoceramides--.

In Claim 10, Col. 19, line 48, after "anionic", insert --surface-active agent--.

In Claim 10, Col. 19, line 48; Claim 13, Col. 19, line 62; and Claim 14, Col. 20, line 2, after "agent" insert --selected from zwitterionic and amphoteric surface-active agents--.

In Claim 10, Col. 19, lines 49-50; Claim 13, Col. 19, lines 62-65; and Claim 14, Col. 20, lines 2-5, delete ", said at least one zwitterionic surface-active agent, or said at least one amphoteric surface-active agent and said at least one zwitterionic surface-active agent".

In Claim 17, Col. 20, line 17; and Claim 18, Col. 20, line 21, after "one" (first occurrence), insert --compound selected from ceramides and glycoceramides--.

In Claim 17, Col. 20, lines 17-18; and Claim 18, Col. 20, lines 21-22, delete "ceramide, at least one glycoceramide, or at least one ceramide and at least one glycoceramide".

UNITED STATES PATENT AND TRADEMARK OFFICE
CERTIFICATE OF CORRECTION

PATENT NO. : 5,661,118
DATED : August 26, 1997
INVENTOR(S) : Daniele Cauwet, et. al.

It is certified that error appears in the above-indentified patent and that said Letters Patent is hereby corrected as shown below:

In Claim 23, Col. 20, line 40, "foe" should read --foam--.

Signed and Sealed this

Eighteenth Day of November 1997

*Attest:*

BRUCE LEHMAN

*Attesting Officer*  *Commissioner of Patents and Trademarks*